US009372118B1

(12) United States Patent
Taplin et al.

(10) Patent No.: US 9,372,118 B1
(45) Date of Patent: Jun. 21, 2016

(54) APPARATUS AND METHOD FOR MULTISPECTRAL BASED DETECTION

(71) Applicant: FluxData, Inc., Rochester, NY (US)

(72) Inventors: Lawrence A. Taplin, Rochester, NY (US); Pano A. Spiliotis, Rochester, NY (US)

(73) Assignee: FluxData, Inc., Rochester, NY (US)

( * ) Notice: Subject to any disclaimer, the term of this patent is extended or adjusted under 35 U.S.C. 154(b) by 0 days.

(21) Appl. No.: 14/314,469

(22) Filed: Jun. 25, 2014

Related U.S. Application Data (63) Continuation of application No. 13/412,875, filed on Mar. 6, 2012, now abandoned.

(60) Provisional application No. 61/449,969, filed on Mar. 7, 2011.

(51) Int. Cl.
G01N 21/25 (2006.01)
G01J 3/51 (2006.01)

(52) U.S. Cl.
CPC .............. *G01J 3/51* (2013.01); *G01N 2223/422* (2013.01)

(58) Field of Classification Search
CPC .............. G01J 3/51; G01J 2003/3836; G01N 2223/422
See application file for complete search history.

(56) References Cited

U.S. PATENT DOCUMENTS

| 4,765,564 | A | * | 8/1988 | Colvocoresses | ............. 244/3.16 |
|---|---|---|---|---|---|
| 5,606,413 | A | * | 2/1997 | Bellus et al. | .................. 356/326 |
| 5,994,150 | A | * | 11/1999 | Challener et al. | ............. 436/518 |
| 7,763,876 | B2 | * | 7/2010 | Banton et al. | .............. 250/559.4 |
| 7,855,876 | B2 | * | 12/2010 | Zhu et al. | ................. 361/679.12 |
| 8,081,311 | B2 | * | 12/2011 | Themelis | ....................... 356/419 |
| 8,379,193 | B2 | * | 2/2013 | Gardner et al. | ................. 356/73 |
| 2003/0109773 | A1 | * | 6/2003 | Samuels et al. | ............... 600/315 |
| 2005/0286048 | A1 | * | 12/2005 | Kitagawa | ...................... 356/318 |
| 2008/0123097 | A1 | * | 5/2008 | Muhammed et al. | ......... 356/419 |
| 2011/0085708 | A1 | * | 4/2011 | Martin et al. | ................. 382/115 |
| 2011/0176048 | A1 | * | 7/2011 | Rockley | ........................ 348/340 |

* cited by examiner

*Primary Examiner* — Kara E Geisel
*Assistant Examiner* — Hina F Ayub
(74) *Attorney, Agent, or Firm* — John M. Hammond; Patent Innovations LLC (57) ABSTRACT

An apparatus for spatially characterizing an illumination source of interest in a scene comprised of at least one optical element configured to form an image on a focal plane; a single plane sensing array comprising at least two types of pixels having different spectral sensitivity bands, the pixels located at spatially non-overlapping regions of the sensing array; a multi-bandpass filter spectrally narrowing light received from the scene within at least two of the different spectral sensitivity bands corresponding to features that distinguish the illumination source of interest from other sources in the scene; and a processor in signal communication with the sensing array and containing an algorithm to interpolate at least two levels of signals received from at least one spatial location on the sensing array and to determine the presence of the specific illumination source of interest from the relative intensities of the two levels.

20 Claims, 6 Drawing Sheets

APPARATUS AND METHOD FOR MULTISPECTRAL BASED DETECTION

CROSS-REFERENCE TO RELATED PATENT APPLICATIONS

This application is a continuation of copending U.S. patent application Ser. No. 13/412,875, filed on Mar. 6, 2012, which claims priority from U.S. provisional patent Application No. 61/449,969, filed Mar. 7, 2011, the disclosures of which are incorporated herein by reference.

BACKGROUND

1. Technical Field

Methods and apparatuses for multispectral detection of substances in a given scene or field of view.

2. Description of Related Art

Successful optical detection of specific materials and substances in a scene is dependent on being able to distinguish the signal signature within received light relating to their reflection, absorption or emission characteristics from those of background sources and noise. Commercially available image sensors with integrated patterned filter arrays provide a convenient means of sensing received light and acquiring multiband data that can be fed through algorithms to examine inter-band relationships for detection-indicating criteria. However, the multiple spectral response bands of these sensors are typically optimized for criteria other than detection of specific materials and substances such as reducing visible artifacts like noise and aliasing. Distinct spectral response bands are usually created by placing a micro-scale pattern of pigment or dye-based filters, commonly called a color filter array (CFA), in front of a photo-detector array that on its own has little or no native wavelength selectivity. The addition of the CFA creates a sensor whereby each photo-detector (pixel) is assigned to just one of a plurality of spectral response band classes by the transmission properties of the CFA disposed above it.

The CFA pattern and the spectral transmittances of its filters are usually designed to produce data that can be converted to accurate color images through a process called demosaicing. In this process the observed signals from the two dimensional array of pixels, each having a specific spectral response, typically peaking in the red, green and blue (RGB) portions of the visible spectrum, are used to create a multiband image where spectral responses for all bands are estimated at all pixel locations. The estimation is often done through linear or non-linear interpolation of the sparse spatial sampling of the CFA pattern. Furthermore, by examining pixel values between spectral response bands, a determination can be made as to whether the light from the scene likely contains a portion of reflected, absorbed or emitted by the material or substance that is to be detected. Methods for examining the intra-band relationships to determine if the material or substance is present require that the observed signal can be distinguished from signals from other sources such as reflections from materials or substances not of interest (background) and noise.

SUMMARY

Our apparatus and method can shift or narrow the spectral peaks of the CFA using a multi-band-pass filter inserted into the optical path of the system so that at least two of the system's spectral response bands correlate with specific absorption, reflection or emission features of the material or substance to be detected, or to the background signal to allow higher detection accuracy and greater false-signal rejection.

The preferred and alternate embodiment of the apparatus and method of multispectral detection overcome the limited choice of commercially available CFA arrays without complex optical assemblies, multiple image sensors or precise alignment of system components.

In accordance with the present disclosure, the problem of instantaneously and passively spatially detecting, quantifying, or classifying specific sources of illumination in a scene is addressed by including in a sensing system and detection method a multi-bandpass optical filter whose design is optimized to modify at least two of the spectral response bands of an array type patterned filter sensor to improve discrimination between spectral features of the illumination source of interest and likely background sources of illumination.

More specifically, according to the present disclosure, an apparatus for spatially characterizing a specific illumination source of interest in a scene is provided. The apparatus is comprised of at least one optical element configured to form an image on a focal plane; a single plane sensing array positioned at the focal plane and comprising at least two types of pixels having different spectral sensitivity bands, the pixels located at spatially non-overlapping regions of the sensing array; a multi-bandpass filter disposed between the scene and the sensing array, the filter spectrally narrowing light received from the scene within at least two of the different spectral sensitivity bands corresponding to spectral absorption, reflection, or emission features that distinguish the illumination source of interest from other illumination sources in the scene; and a processor in signal communication with the sensing array and containing an algorithm to interpolate at least two levels of signals received from at least one spatial location on the sensing array and to determine the presence of the specific illumination source of interest from the relative intensities of the two levels.

The algorithm may include determining the quantity of the specific illumination source of interest present in the scene. In circumstances where the scene may include a plurality of illumination sources of interest, the algorithm may include classifying the specific illumination sources of interest present in the scene.

There are numerous applications for the Applicants' apparatus. For example, if the illumination source of interest is human skin, the spectral sensitivity bands of the at least two types of pixels may be provided corresponding to the spectral absorption and reflection from hemoglobin or melanin. If the illumination source of interest is a weapon discharge, and the spectral sensitivity bands of the at least two types of pixels may be provided corresponding to the emission from the discharge of the weapon.

The multi-bandpass filter may be disposed between the at least one optical element and the scene, or between the at least one optical element and the sensing array. The multi-bandpass filter may be a dichroic reflector configured to reflect light towards the sensing array. The peak wavelengths of the multi-bandpass filter may be made adjustable by rotation of the filter to a non-parallel position with respect to the focal plane.

The apparatus may further include an optical sensor in signal communication with the processor. In such a configuration, the algorithm may include processing signals received from the optical sensor to better estimate a range of expected responses that positively or negatively indicate detection of the illumination source of interest. Detection accuracy of the apparatus is thereby improved. The optical sensor may be a diffuse light sensor and/or a directional light sensor.

Also according to the present disclosure, a method for spatially characterizing a specific illumination source of interest in a scene is further provided. The method comprises directing light from the scene through a multi-bandpass filter to narrow the light within at least two different spectral sensitivity bands that distinguish the illumination source of interest from other illumination sources in the scene. The filtered light is projected to form an image of the scene onto a single plane sensing array comprising at least two types of pixels having different spectral sensitivity bands corresponding to spectral absorption, reflection, or emission features that distinguish the illumination source of interest from other illumination sources in the scene. The pixels may be located at spatially non-overlapping regions of the sensing array. The signals from the sensing array are processed to interpolate at least two levels of signals received from at least one spatial location on the sensing array and to determine the presence of the specific illumination source of interest from the relative intensities of the two levels.

The method may include determining the quantity of the specific illumination source of interest present in the scene. In circumstances where the scene may include a plurality of illumination sources of interest, the method may include classifying the specific illumination sources of interest present in the scene. If the illumination source of interest is human skin, the method may include detecting the spectral absorption and reflection from hemoglobin or melanin. If the illumination source of interest is a weapon discharge, the method may include detecting the emission of the discharge.

BRIEF DESCRIPTION OF THE DRAWINGS

The present disclosure will be provided with reference to the following drawings, in which like numerals refer to like elements, and in which.

The present invention will be described in connection with a preferred embodiment. However, it is to be understood that there is no intent to limit the invention to the embodiment described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements.

Figure 1:
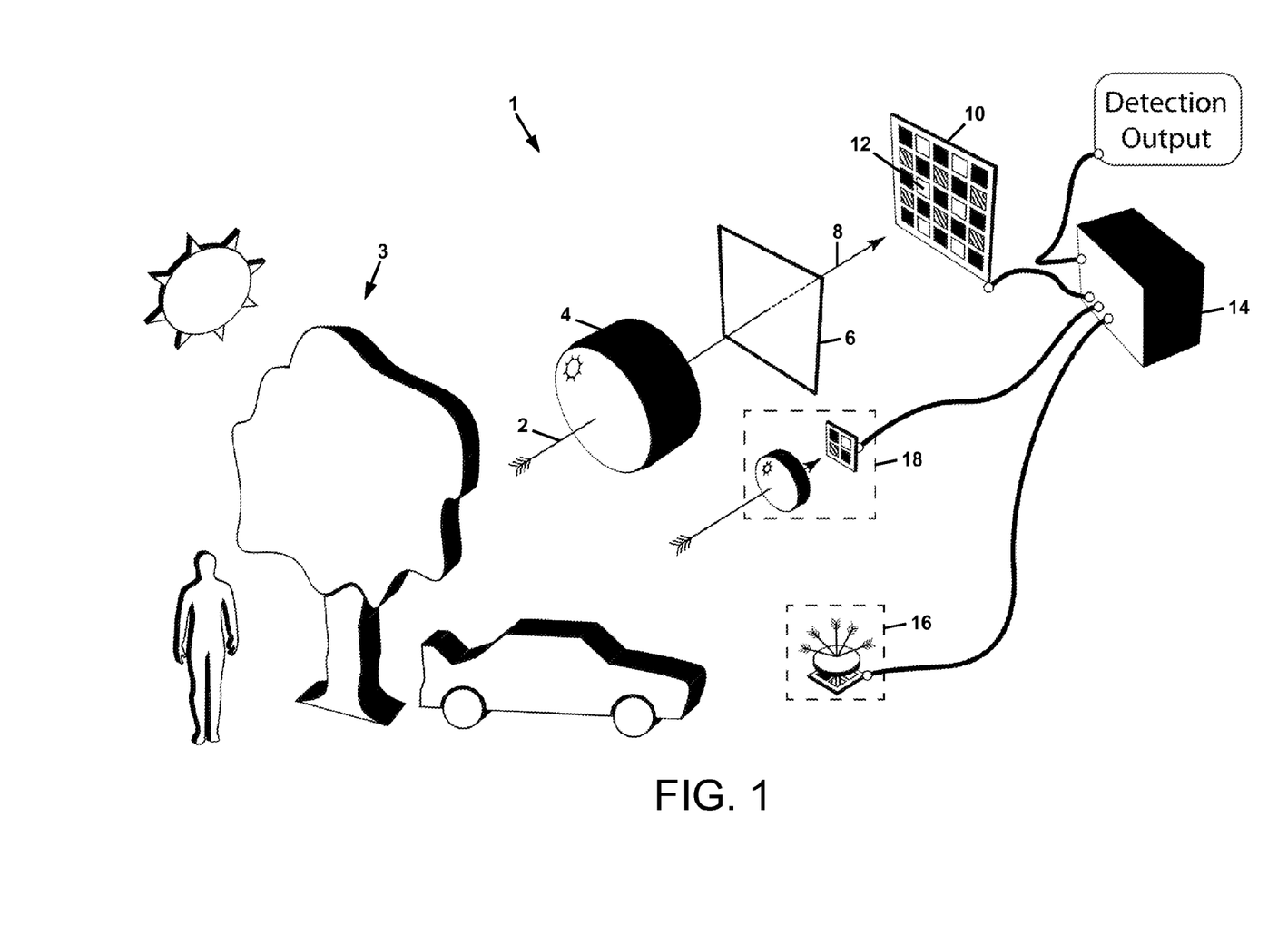
FIG. 1 is an illustration of an embodiment of the Applicants' apparatus for multispectral based detection.

FIG. 1 is an illustration of an embodiment of the Applicants' apparatus 1 for multispectral based detection. The apparatus 1 includes at least one optical element 4 configured to form an image on a focal plane. Incoming light reflected 2 or emitted 2 from a scene 3 that may contain the material or substance to be detected is collected by light collection optics 4 (typically reflective, refractive or diffractive) and passes through a multi-band-pass filter 6. The filter 6 is disposed between the scene 3 and the sensing array 10. The filter 6 spectrally narrows light 2 received from the scene 3 within at least two of the different spectral sensitivity bands corresponding to spectral absorption, reflection, or emission features that distinguish the illumination source of interest from other illumination sources in the scene 3.

The filtered light 8 is projected as an image on a two-dimensional, i.e., single plane sensor array 10, which is covered with a color filter array (CFA) 12. The sensor array 10 is comprised of at least two types of pixels having different spectral sensitivity bands. The pixels are located at spatially non-overlapping regions of the sensing array 10. Optionally, auxiliary single (not shown) or multiband light sensors 16 and 18 can be used to collect additional information about average scene radiance and irradiance. Each of these sensors may have spectral response bands different from the image sensor array 10 and CFA 12. They can be used to automatically set parameters of a spectral detection algorithm, or perform scene white balancing for improved detection accuracy. Image and sensor data captured by the sensor array 10 is stored and processed on a computer or processor 14 in signal communication with the sensor array 10. The processor 14 contains the algorithm, which interpolates at least two levels of signals received from at least one spatial location on the sensing array 10 and determines the presence of the specific illumination source of interest from the relative intensities of the two levels. The processor 14 may be remotely located, and in wireless signal communication with the sensing array 10.

The algorithm may include determining the quantity of the specific illumination source of interest present in the scene 3. In circumstances where the scene may include a plurality of illumination sources of interest, the algorithm may include classifying the specific illumination sources of interest present in the scene 3.

In one application of the Applicants' apparatus, the illumination source of interest may be human skin. To detect the human skin, the spectral sensitivity bands of the at least two types of pixels of the sensing array 10 may be provided corresponding to the spectral absorption and reflection from hemoglobin or melanin. In another application, the illumination source of interest may be a weapon discharge, in which case, the spectral sensitivity bands of the at least two types of pixels may be provided corresponding to the emission from the discharge of the weapon. Other applications for detection and characterization of illumination sources of interest are contemplated.

Figure 2A:
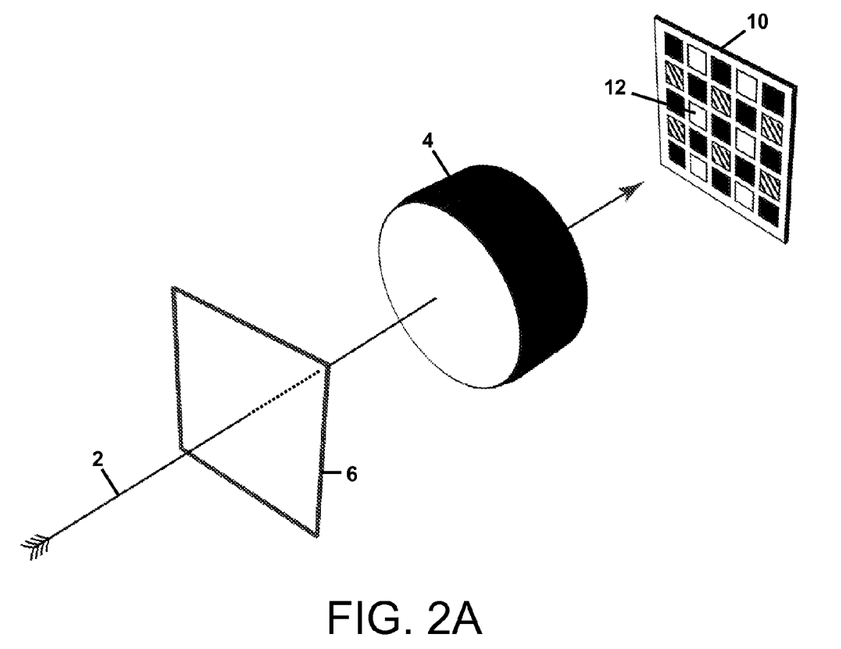
FIG. 2A is an illustration of a first alternative arrangement of certain components of the apparatus of FIG. 1, operating in a transmission mode.

FIG. 2A shows a first alternative embodiment where the multi-band-pass filter 6 is placed in front of the light collection optics 4. This configuration is advantageous when a long focal length lens is used for the collection optics 4. In such circumstances, the incident light 2 passing through the multi-band-pass transmission filter 6 will subtend a small cone (not shown). If transmission of the multi-band-pass filter 6 varies with incident angle, the filter 6 can be rotated in front of the lens (not shown) of the collection optics 4, thereby tuning the system's spectral response bands to adjust them toward, or search for, those bands that are optimal for detection of the material or substance of interest in the scene 3 (FIG. 1).

Figure 2B:
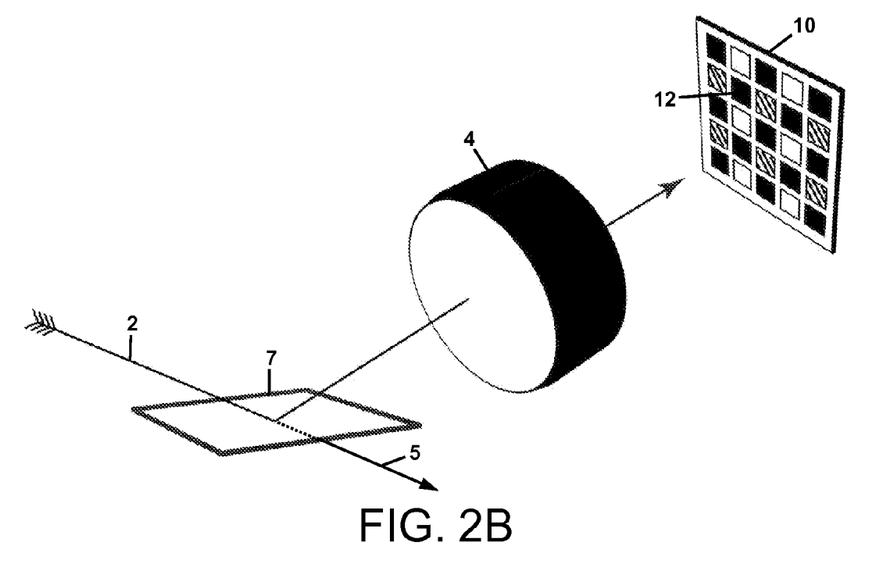
FIG. 2B is an illustration of a second alternative arrangement of certain components of the apparatus of FIG. 1, operating in a reflection mode.

FIG. 2B shows a second alternative embodiment where a multi-band-pass reflection filter 7 is used instead of a transmission filter 6 (FIGS. 1 and 2A). In this configuration, the incident illumination 5 that is not reflected or absorbed could be directed to an alternate sensor or optics (not shown) via transmission through the filter 7. The multi-bandpass filter 7 may be a dichroic reflector configured to reflect light towards the sensing array 10.

Figure 3:
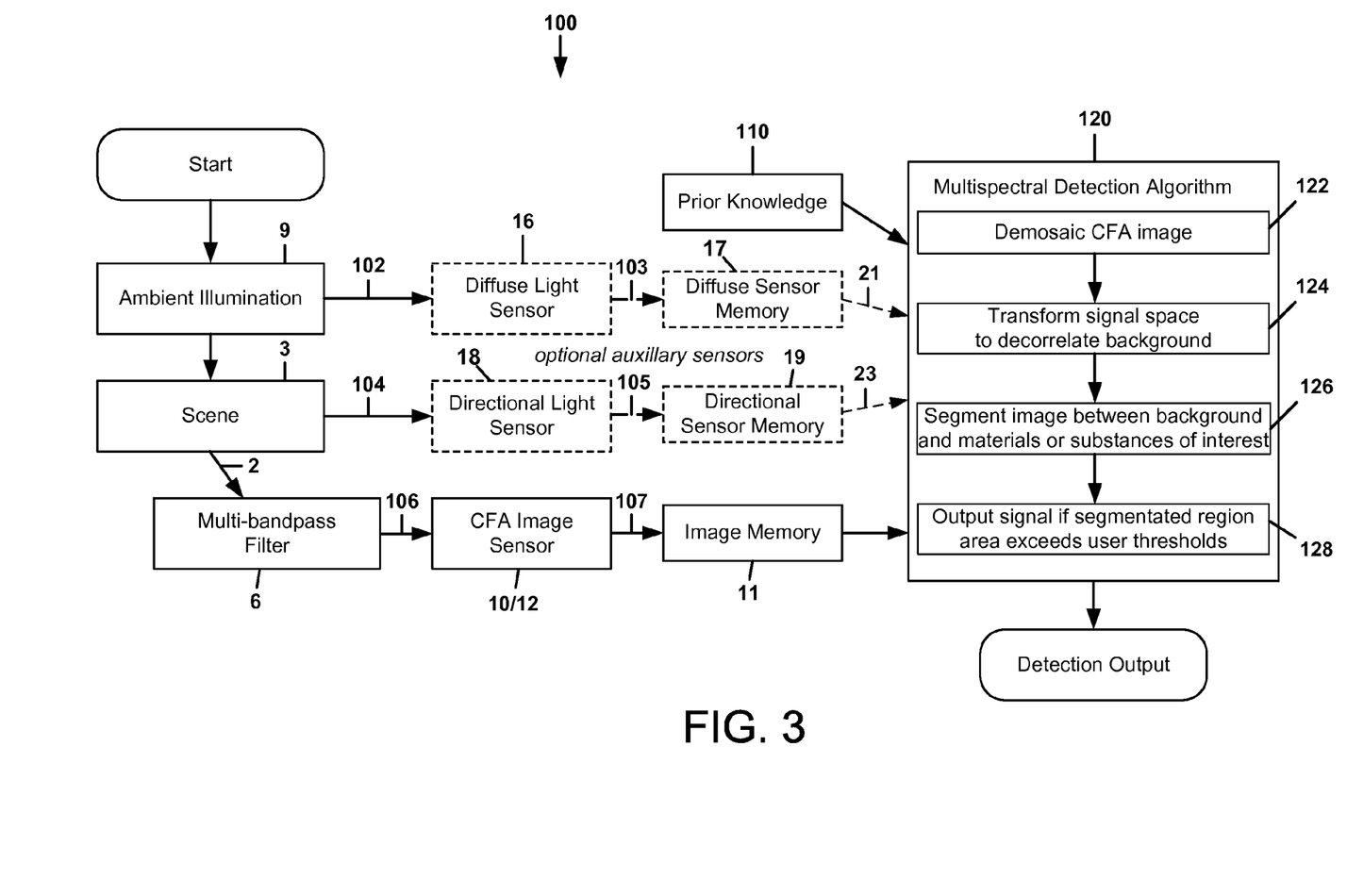
FIG. 3 is a flowchart depicting a method of multispectral based detection.

FIG. 3 is a flowchart depicting a method 100 of multispectral based detection in which detection of a substance or material of interest in a scene 3 (FIG. 1) can be performed. In method 100, ambient illumination 9 in the scene 3 is reflected by various objects in the scene 3. The reflected light may be directly measured 102 with an optional one or multiple band diffuse light sensor 16 of the apparatus 1 (FIG. 1). The diffuse light sensor 16 may include a memory 17 for storing 103 the reflected light data. The amount of light modulated by reflection, absorption and emission from objects in the scene 3 that impinges upon an optional one or multi-band directional light sensor 18 may also be measured 104 and stored 105 in a memory 19 of the sensor 18. Additionally, light 2 exiting the scene 3 in the direction of the light collection optics 4 (FIG. 1) is passed through a multi-band-pass filter 6 and detected 106 by the image sensor 10 with a color filter array 12. The image sensor 10 may include a memory 11 which records 107 image data.

A multispectral detection algorithm 120 is used to determine if materials or substances of interest are present in the scene 3, as described previously herein. The algorithm is defined based upon prior knowledge 110 of the expected response to illumination from materials and substances of interest, and of background sources in the scene 3 under the conditions deduced from the optional auxiliary sensors 16 and/or 18, or from the image data stored in memory 11. The algorithm may be stored in a memory (not shown) of the computer 14, and executed by a central processing unit (not shown) of the computer 14. The memories 17 and 19 of the diffuse and directional light sensors 16 and 18, and the memory 11 of the image sensor 10 may also be integrated into the computer 14; or these memories may be parts of their respective sensors.

More specifically, in certain embodiments, the detection algorithm 120 may begin by demosaicing 122 the CFA image data stored in memory. That is, for one or more spatial locations of interest, at least two or more of the spectral responses must be known by their coincidence with sensing array spatial locations or interpolated from spectral responses at an adjacent array position. Next, incoming signals may be mathematically and statistically transformed 124 in a way to separate the response of the material or substance of interest from the background signal, for example, by independent component analysis (ICA) or principal component analysis (PCA. The transformed image data may then be segmented 126 between background and materials or substances of interest based on intra-band pixel values and parameters, which are based on the auxiliary sensor data 21 and 23 and prior knowledge 110. Lastly, if the area or signal level of segmented regions exceeds a user-defined threshold, a detection signal may be outputted 128. Thus, rather than producing spectral images as performed by known spectral imaging systems, algorithm 120 enables the Applicants' system 1 to produce instantaneous maps of the probability of presence and/or quantity of a particular substance in a particular scene. Such maps may be thresholded if the purpose of the system 1 in a given application is detection of the substance.

It is to be understood that the steps 122-128 of the multispectral detection algorithm 120 shown in FIG. 3 are representative of one embodiment of the detection algorithm 120. Individually they may be omitted, reordered, or combined to form alternative embodiments.

Figure 4:
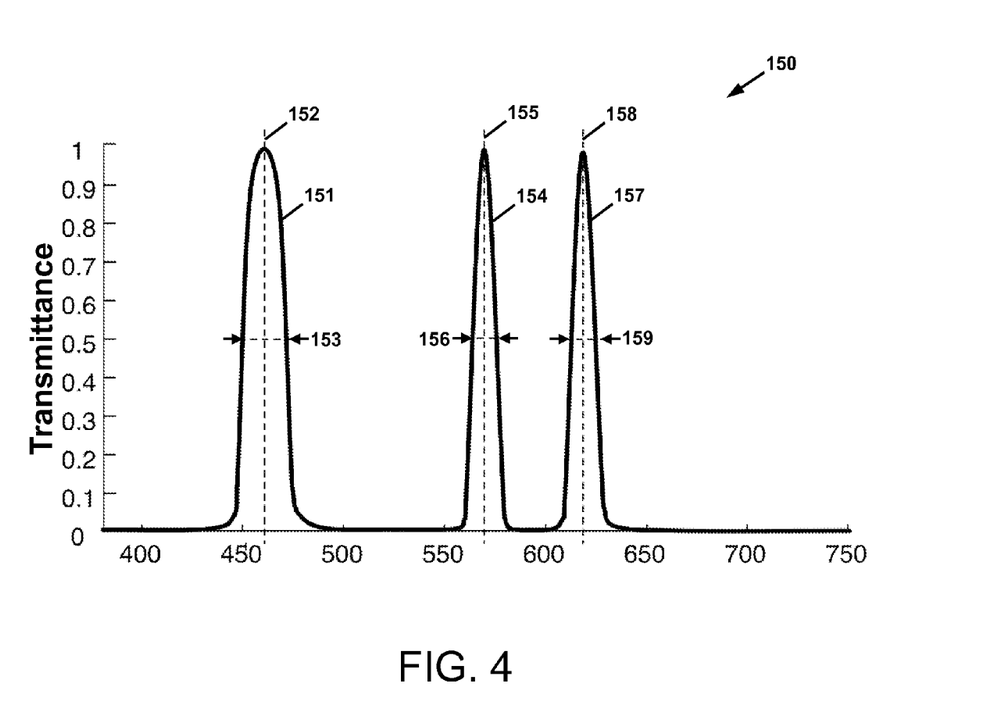
FIG. 4 is a graphical illustration of the transmittance parameters of a multi-band-pass filter of the Applicants' apparatus matched to an RGB color filter array.

The spectral transmission or reflectance of the multi-band-pass filter 6 (FIG. 1) or filter 7 (FIG. 2B) may be described in a parameterized way. FIG. 4 is a graphical illustration of the transmittance parameters of a multi-band-pass filter of the Applicants' apparatus matched to a red-green-blue (RGB) color filter array. The total number of features in the graph 150 is a multiple of the number of distinct spectral response band pixel classes created by the CFA pattern. For an RGB color filter array, there are three features or peaks 151, 154, and 157.

Each feature may be characterized by two parameters. The first parameter type is center wavelength (CW) for each feature/peak, i.e. center wavelengths 152, 155, and 158 for peaks 151, 154, and 157, respectively. The second parameter type is the full-width at half of the maximum height (FWHM) for each peak/feature, i.e. FWHMs 153, 156, and 159 for peaks 151, 154, and 157, respectively.

If the widths of spectral band-passes vary greatly, or the expected ratio of signals is known, then the height of each band-pass can also be specified to maximize dynamic range. Additionally, the transition wavelengths surrounding the features can form different shaped band-passes such as a Gaussian or rectangle. These shapes can be parameterized by describing the slope of the transmission curve at the FWHM points. Accordingly, for the instant RGB CFA sensor-based multispectral detection system, at least six parameters for the multi-band-pass filter must be defined: three center wavelengths 152, 155, and 158; and three full-width at half max values 153, 156, and 159.

Figure 5A:
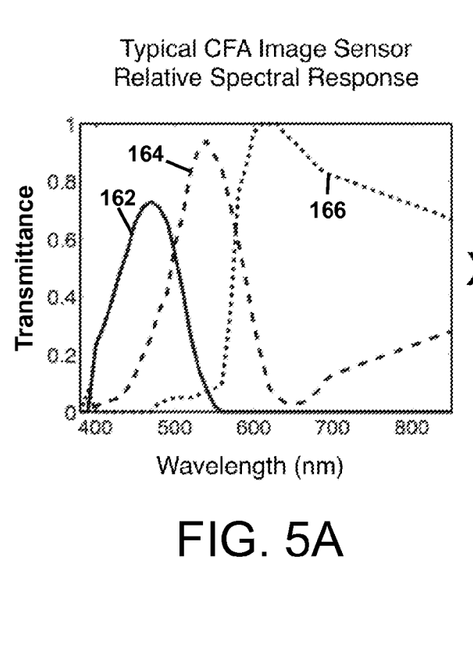
FIG. 5A is depicts the response of a typical RGB color filter array CCD image sensor of the Applicants' apparatus.

FIG. 5A depicts the response of a typical RGB color filter array CCD image sensor, which may be used as sensor 10 in the apparatus 1 (FIG. 1). The respective blue, green, and red sensitivities 162, 164, and 166 are shown.

It is noted that the green and red response bands 164 and 166 have significant spectral response in the near infrared (NIR) region around 800 nm. In conventional color imaging, such as with commercial digital cameras, this response is typically modulated with a short pass or visible band-pass filter, since the information carried in this region correlates poorly with human color vision. However, in the instant multispectral detection system, the multi-band-pass filter 6 (FIG. 1) or 7 (FIG. 2B) is optimized for a different purpose. In many instances, spectral response in the NIR region may be desirable, and thus short pass or visible band-pass filters in such instances should not be used.

Figure 5B:
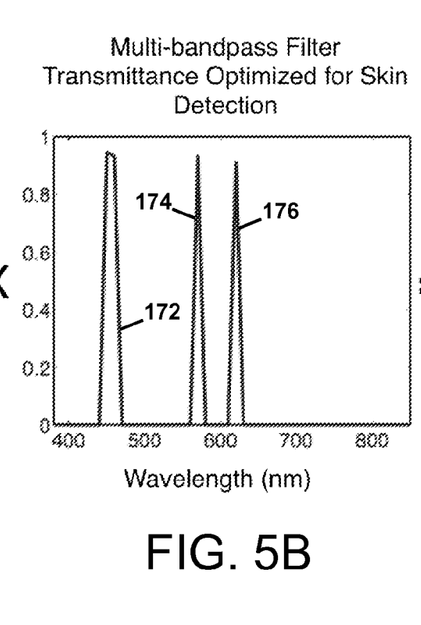
FIG. 5B depicts the transmittance of a filter optimized for image-based multispectral detection of human skin using an RGB color filter array sensor.

It has been further recognized by the Applicants that the transmittance of a multi-band-pass filter 6 may be optimized for detection of the particular substance which is desired to be confirmed as present or not present in a particular scene by using numerical simulation of the system's expected performance and a search of the parameterized description of the filter's transmittance. It is to be understood that the term "scene" as used here can be any field of view of the apparatus 1, such as the outdoor scene 3 of FIG. 1, or a close-up view of a particular object, in which a surface of the object is imaged. By way of illustration, and not limitation, FIG. 5B depicts the transmittance of a multi-band-pass filter optimized for multispectral based detection of human skin using an RGB color filter array sensor. A first spectral peak 176 at about 620 nm is selected to match a spectral absorption band of oxygenated hemoglobin. Peaks 172 and 174 are selected for effective background rejection.

Figure 5C:
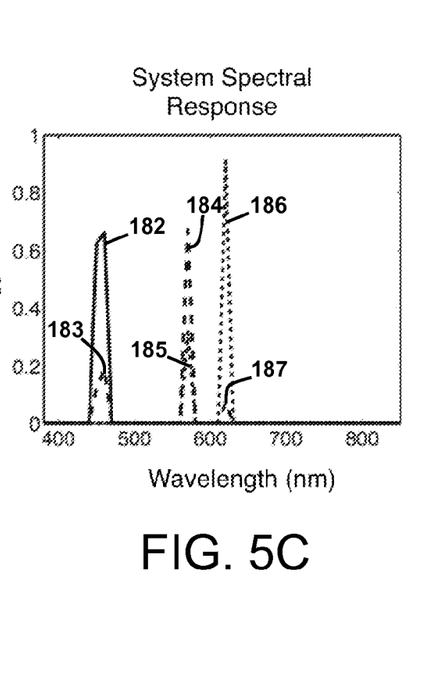
FIG. 5C depicts "cross-talk" that may occur between channels of a multi-bandpass filter used in the apparatus.

Referring to FIG. 5C, it can be seen that narrow transmission bands of the filter cause the peaks 182, 184, and 186 of the spectral response of the system to be similarly narrow. However, because the spectral response bands of the CFA filter as shown in FIG. 5A overlap in the transmittance regions of the multi-band-pass filter, there are significant cross-talk peaks 183, 185, and 187 between channels.

Figure 6:
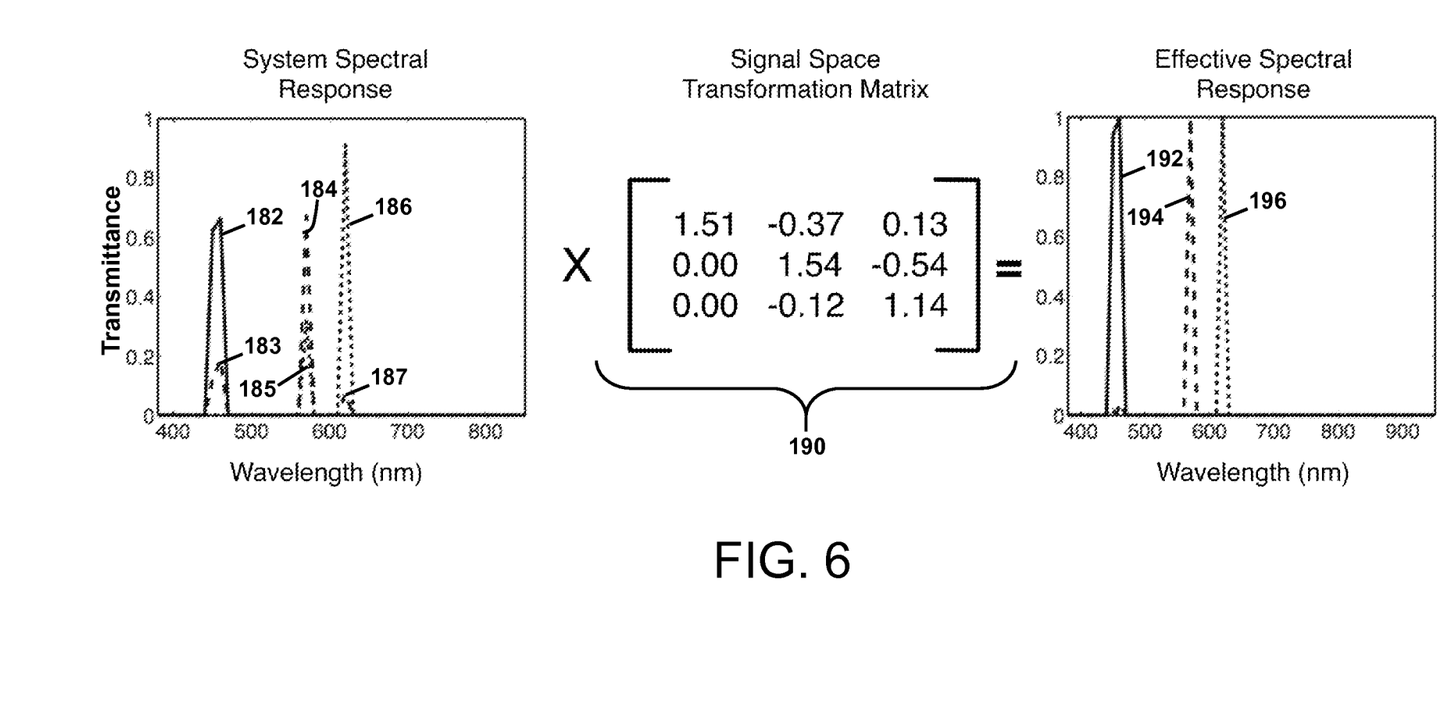
FIG. 6 depicts a method for removing cross-talk by transforming signals from the systems through a three-by-three matrix.

FIG. 6 depicts a method for removing such cross-talk. The signals 182-187 from the system are transformed through a three-by-three matrix multiplication 190 to achieve effectively the spectral responses 192, 194, and 196 with minimal cross-talk. In this case, the transformation matrix is also defined such that the spectral response curves 192, 194, and 196 are normalized to a peak height of unity. The matrix was generated using singular value decomposition (SVD) of the expected response, but could be tuned empirically based on the observed response of the system to known input stimuli. In other embodiments, the matrix could be scaled such that the response area for a particular illuminant integrates to unity, in which case the system would be white-balanced for that illuminant.

It is to be understood that in spectral imaging, although most CFA image sensors are either charge coupled devices (CCD) or complementary metal-oxide-semiconductor (CMOS) devices, and most color filter arrays are RGB arrays, the Applicants' multispectral detection system may also be provided with other types of detectors or those sensitive to non-visible radiation, and in configurations in which the color filter array pattern creates more than three spectral response bands, or non-RGB response bands (such as RGBW, CMY, etc.). Additionally, optical thin films or alternate technologies may be used to create the color filter array.

It is, therefore, apparent that there has been provided, in accordance with the present invention, a method and apparatus for multispectral based detection. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

We claim:

1. An apparatus for spatially characterizing a specific illumination source of interest in a scene, the apparatus comprising:
    a) at least one optical element configured to form an image of the scene including the specific illumination source of interest on a focal plane;
    b) a single plane sensing array covered by a color filter array and having a field of view, and positioned at the focal plane and comprising at least two types of pixels having different spectral sensitivity bands, the pixels located at spatially non-overlapping regions of the sensing array;
    c) a multi-bandpass filter disposed between the scene and the sensing array, the filter separated from the sensing array and spectrally transmitting light received from the scene in pass bands, the pass bands having a maximum peak transmissivity corresponding to at least one of the at least two different pixel spectral sensitivity bands, and the different pixel spectral sensitivity bands corresponding to spectral absorption, reflection, or emission features that distinguish the specific illumination source of interest from other illumination sources in the scene;
    d) a secondary optical sensor having different spectral sensitivity bands than the single plane sensing array and fewer total sensing elements; and
    e) a processor in signal communication with the sensing array and the optical sensor and containing an algorithm executable by the processor to process individual image data received from the sensing array, and for each individual image defined by the received image data, to interpolate at least two levels of signals received from at least one spatial location on the sensing array, and to process signals received from the secondary optical sensor to estimate a range of expected responses that indicate detection of the illumination source of interest, and to determine the presence of the specific illumination source of interest from the relative intensities of the at least two levels and the expected response range.

2. The apparatus of claim 1, wherein the algorithm includes determining the quantity of the specific illumination source of interest present in the scene.

3. The apparatus of claim 1, wherein the scene includes a plurality of illumination sources of interest, and the algorithm includes classifying the specific illumination sources of interest present in the scene.

4. The apparatus of claim 1, wherein the spectral sensitivity bands of the multi-bandpass filter correspond to spectral absorption or reflection features of hemoglobin or melanin.

5. The apparatus of claim 1, wherein the spectral sensitivity bands of the multi-bandpass filter correspond to the emission from a discharge of a weapon.

6. The apparatus of claim 1, wherein the multi-bandpass filter is disposed between the at least one optical element and the scene.

7. The apparatus of claim 1, wherein the multi-bandpass filter is disposed between the at least one optical element and the sensing array.

8. The apparatus of claim 1, wherein the multi-bandpass filter is a dichroic reflector configured to reflect light towards the sensing array.

9. The apparatus of claim 1, wherein peak wavelengths of the multi-bandpass filter are adjustable by rotation of the filter to a non-parallel position with respect to the focal plane.

10. The apparatus of claim 1, wherein the optical sensor is a diffuse light sensor having a field of view, and wherein the scene includes sky, and the field of view of the sensor is the sky.

11. The apparatus of claim 1, wherein the optical sensor is a directional light sensor having a field of view, and wherein the field of view of the sensor and the field of view of the single plane sensing array are the same field of view.

12. The apparatus of claim 1, wherein the scene is an outdoor scene containing the specific illumination source of interest and the other illumination sources.

13. The apparatus of claim 1, wherein the algorithm further comprises instructions to demosaic the individual image data, to separate one of the at least two levels of signals representative of a material of interest in the scene from another of the at least two levels of signals representative of a background of the scene, to segment between the background and the material of interest based on intra-band pixel values and parameters, and if the signal of a segmented region representative of a material of interest exceeds a user-defined threshold, outputting a signal indicative of detection of the material of interest.

14. A method for spatially characterizing a specific illumination source of interest in a scene, the method comprising:
   a) predetermining wavelengths of light corresponding to the specific illumination source of interest that may be present in the scene;
   b) directing light from the scene through a multi-bandpass filter to cause narrowing of the light within at least two different spectral sensitivity bands that distinguish the illumination source of interest from other illumination sources in the scene;
   c) projecting the filtered light to form an image of the scene, including the specific illumination source of interest, through a color filter array covering a single plane sensing array, the single plane sensing array separate from the multi-bandpass filter and comprising at least two types of pixels having different spectral sensitivity bands corresponding to spectral absorption, reflection, or emission predetermined wavelengths that distinguish the illumination source of interest from other illumination sources in the scene; and
   d) processing signals defining individual images from the sensing array, and for each individual image, interpolating at least two levels of signals received from at least one spatial location on the sensing array and determining the presence of the specific illumination source of interest from the relative intensities of the two levels.

15. The method of claim 14, further comprising determining the quantity of the specific illumination source of interest present in the scene.

16. The method of claim 14, wherein the scene includes a plurality of specific illumination sources of interest, and the method includes predetermining wavelengths of light corresponding to each illumination source of the plurality of illumination sources of interest and classifying the specific illumination sources of interest present in the scene.

17. The method of claim 14, wherein the scene includes human skin, and the illumination source of interest is at least one of hemoglobin or melanin contained in human skin, and the method includes predetermining wavelengths of light corresponding to spectral absorption and reflection from the at least one of the hemoglobin or melanin, and detecting the spectral absorption and reflection from the at least one of the hemoglobin or melanin present in the human skin in the scene.

18. The method of claim 14, wherein the illumination source of interest in the scene is a weapon discharge, and the method includes predetermining wavelengths of light corresponding to the weapon discharge detecting the emission of the discharge present in the scene.

19. The method of claim 14, further comprising adjusting peak wavelengths of the multi-bandpass filter.

20. An apparatus for spatially characterizing a specific illumination source of interest in a scene, the apparatus comprising:
   a) at least one optical element configured to form an image of the scene including the specific illumination source of interest on a focal plane;
   b) a single plane sensing array covered by a color filter array, and positioned at the focal plane and comprising at least two types of pixels each having different spectral sensitivity bands and a range of sensitivities which do not overlap at least one of the sensitivity bands of at least one other pixel type, wherein the pixels are located at spatially non-overlapping regions of the sensing array;
   c) a multi-bandpass filter disposed between the scene and the sensing array, the filter separated from the sensing array and spectrally narrowing light received from the scene within at least two of the different spectral sensitivity band ranges corresponding to predetermined spectral absorption, reflection, or emission features that distinguish the specific illumination source of interest from other illumination sources in the scene; and
   d) a processor in signal communication with the sensing array and containing an algorithm executable by the processor to process individual image data received from the sensing array, and for each individual image defined by the received image data, to interpolate at least two levels of signals received from at least one spatial location on the sensing array and to determine the presence of the specific illumination source of interest from the predetermined spectral absorption, reflection, or emission features of the specific illumination source of interest and from the relative intensities of the two levels.

* * * * *